United States Patent [19]

Nakamura et al.

[11] Patent Number: 4,920,413
[45] Date of Patent: Apr. 24, 1990

[54] BLOOD-VESSEL ENDOSCOPE SYSTEM FOR STORING A FROZEN PICTURE IN SYNCHRONIZATION WITH HEART PULSATION

[75] Inventors: Ichiro Nakamura, Kokubunji; Naruto Shinkai, Tokyo, both of Japan; David Barlow, Hicksville; Akio Nakada, Lake Success, both of N.Y.

[73] Assignee: Olympus Optical Co., Ltd., Tokyo, Japan

[21] Appl. No.: 317,247

[22] Filed: Feb. 28, 1989

[51] Int. Cl.⁵ .......................... A61B 1/06; H04N 7/18
[52] U.S. Cl. ............................................. 358/98; 128/6
[58] Field of Search ................... 358/98, 100, 111, 93, 358/110; 128/4, 6, 710, 712, 654, 653; 378/43, 63; 364/413.13

[56] References Cited

U.S. PATENT DOCUMENTS

| | | | |
|---|---|---|---|
| 4,517,963 | 5/1985 | Michel | 128/6 |
| 4,743,966 | 5/1988 | Matsuo | 128/6 X |
| 4,807,026 | 2/1989 | Nishioka et al. | 358/98 |

FOREIGN PATENT DOCUMENTS

| | | |
|---|---|---|
| 0119614 | 8/1987 | European Pat. Off. |
| 59-172621 | 9/1984 | Japan |
| 61-80218 | 4/1986 | Japan |

OTHER PUBLICATIONS

"Measurement of Blood Pressure"; Geddes; Yearbook of Medical Publishers, Chicago; Oct. '82; pp. 42-44.

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

A blood-vessel endoscope system has an endoscope to be inserted into a blood vessel in a living body and a frozen-picture memorizing device connected to the endoscope, and is capable of storing a frozen picture when a release switch is actuated. The system is provided with a frozen-picture memorization controlling device so that a frozen picture free from a large blur may be stored in synchronization with the signal output from a heart pulsation measuring device for measuring the heart pulsation of the living body and at the timing that the action of a myocardium is reduced.

13 Claims, 9 Drawing Sheets

ECG. SIG.

STANDARD PULSE

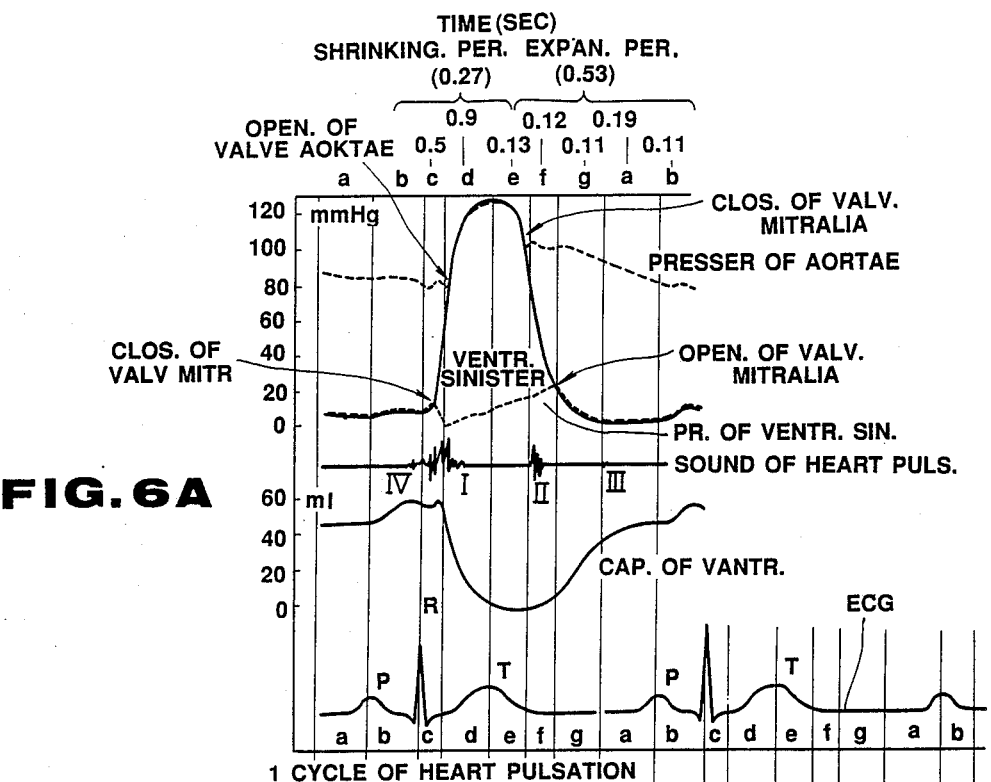
FIG. 6A
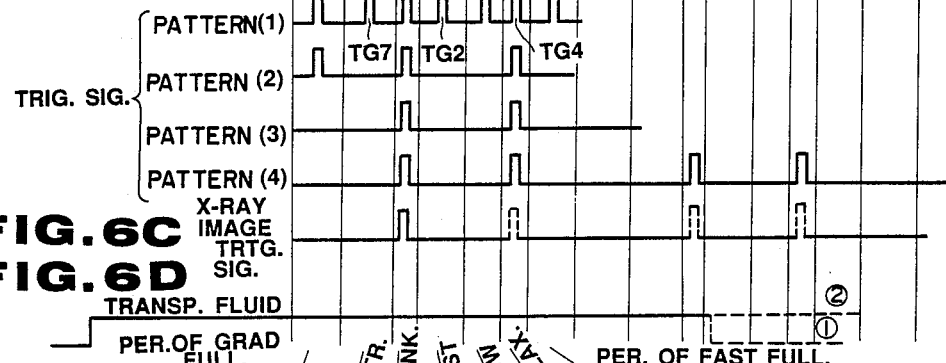
FIG. 6B
FIG. 6C
FIG. 6D
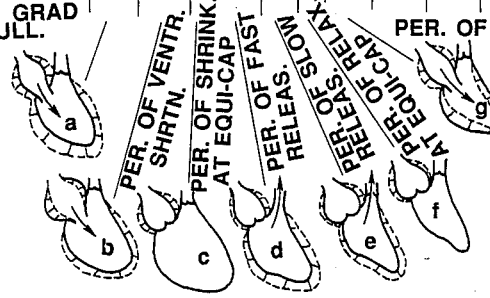
FIG. 6E

FIG. 8
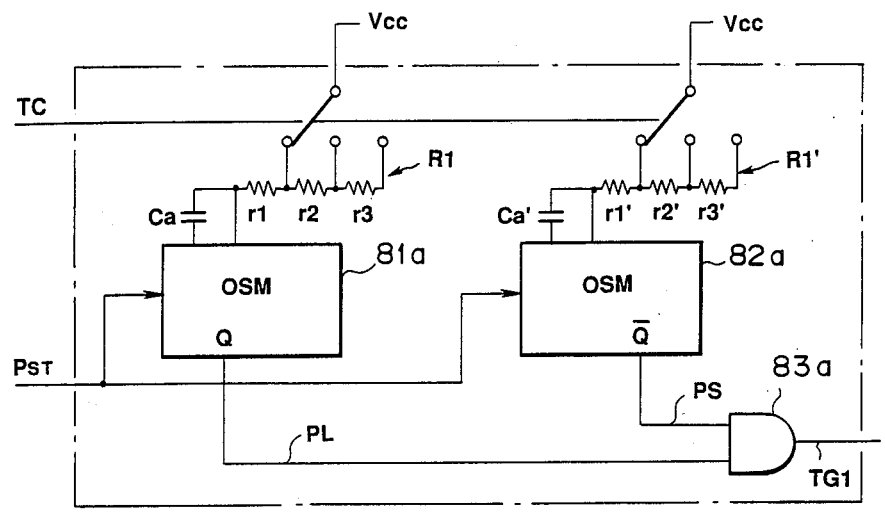
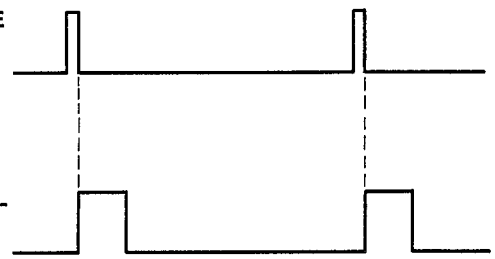
FIG. 9a ST. PULSE PST
FIG. 9b OUTPUT PL OF Q
FIG. 9c OUTPUT PS OF $\overline{Q}$
FIG. 9d OUTPUT TG1 OF AND CC.

FIG.10a FIG.10b
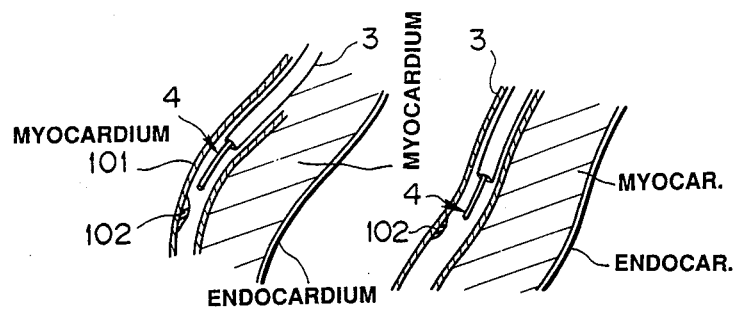
FIG.10c FIG.10d
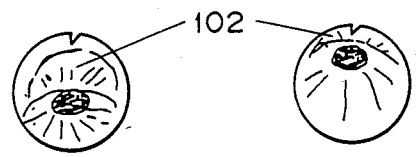
FIG.12
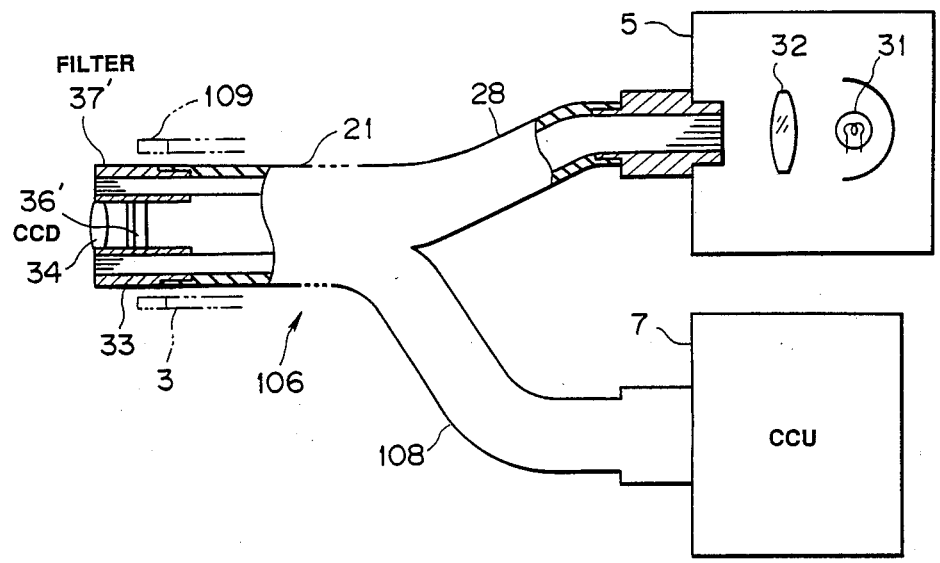

BLOOD-VESSEL ENDOSCOPE SYSTEM FOR STORING A FROZEN PICTURE IN SYNCHRONIZATION WITH HEART PULSATION

BACKGROUND OF THE INVENTION

1. Field of the Invention

The present invention relates to a blood-vessel endoscope system which is arranged to store a frozen picture in synchronization with heart pulsation.

2. Description of the Related Art

In recent years, endoscopes have been widely used which can be inserted into cavities in living bodies to observe internal organs without any need to substantially cut the living bodies or which can be combined, as required, with medical instruments to observe internal organs in the living bodies.

In general, endoscopes having different constructions are prepared for individual applications.

For example, when the digestive system is to be observed, an endoscope having a relative large diameter is prepared. On the other hand, when the interior of a blood vessel is to be observed, a blood-vessel endoscope having a sufficiently small diameter is used.

As will be described later, during observation or examination using such an endoscope, an endoscopic image is commonly stored/recorded for the purpose of detailed examinations which will be performed later.

If an operator applies the aforesaid blood-vessel endoscope to a portion, such as a coronary artery, which moves vehemently, the operator will encounter the problem that it is difficult to obtain a frozen picture without any large blur by image recording using the blood-vessel endoscope.

An example of a prior art which is close to the present invention is disclosed in Japanese Patent Laid-open No. 80218/1986.

In accordance with the proposal made by the prior art, a gap, which serves as a fluid path, is formed between a tubular member and a cover member for covering and connecting an image guide and a light guide, and the gap or fluid path is connected to a fluid supplying means. The operating timing of a light source for supplying illumination light to the fluid supplying means and the light guide, as well as the operating timing of image memorizing means for recording an optical image transferred through the image guide are placed under electronic control.

After a transparent fluid has been injected from the fluid supplying means into an opaque portion such as a blood vessel, illumination light is transferred from the light source and the image memorizing means is activated. Thus, it is possible to efficiently obtain an observation image even in an opaque liquid.

However, if the arrangement disclosed by the aforesaid prior art is used to obtain a frozen picture of a portion such as a coronary artery whose cardiac muscle moves vehemently, the field of view may be assured but the obtained frozen picture will blur. That is to say, since, in the prior art arrangement, the release timing of a frozen picture is not synchronized with the timing at which the motion of a blood vessel becomes small, the resultant frozen picture will blur. Also, in a blood vessel which shows a vehement motion, the relative position between the blood vessel and the endoscope cannot be fixed. Accordingly, even if a frozen picture of such a blood vessel is imaged, a portion of interest may not be imaged within the frozen picture.

Since the prior art involves the disadvantage described above, it is necessary to carry out imaging again and again in order to obtain the frozen picture required. As a result, a burden imposed on an operator and a patient increases and an additional amount of perfusate must be prepared.

The specification of Japanese Patent Laid-open No. 172621/1984 (or EP Pub. No. 0119614) describes the following arrangement. The leading end of a fiber scope is provided with a fluid sensor for the purpose of measuring the flow rate of an opaque fluid, and a transparent fluid is injected in accordance with the flow rate detected by the sensor so as to obtain an image to be observed.

The arrangement of this prior art is such that the flow rate of transparent fluid is determined by the flow rate of blood. In addition, the specification of the prior art includes a description to the effect that the timing of injecting the transparent fluid is determined by utilizing heart pulsation. However, the description is made with respect to the timing at which the supply of the transparent fluid can be decreased, and the prior art arrangement does not include any means for storing a frozen picture. Accordingly, the aforesaid prior art does not propose or suggest any arrangement which makes it possible to provide a frozen picture without any large blur.

SUMMARY OF THE INVENTION

It is an object of the present invention to provide a blood-vessel endoscope system which makes it possible to obtain a frozen picture without any large blur even when a portion, such as a coronary artery, which shows a large motion is imaged.

It is another object of the present invention to provide a blood-vessel endoscope system which makes it possible to obtain a frozen picture which enables easy and rapid diagnosis.

It is still another object of the present invention to provide a blood-vessel endoscope system which makes it possible to obtain the required number of endoscopic images in a short time and which does not need a large amount of perfusate.

To achieve the above objects, in accordance with the present invention, there is provided a blood-vessel endoscope system which includes an electronic endoscope arranged to project illumination light from the leading end of an inserting section, capable of being inserted into a blood vessel, and to thereby image a portion illuminated by the illumination light by means of an imaging device, a heart-pulsation measuring device means for measuring the heart pulsation of a patient, a frozen-picture memorizing device capable of storing as a frozen picture, an image obtained by the imaging device, and a controlling device for controlling the storing operation of the frozen-picture memorizing device in synchronization with a predetermined timing of the heart-pulsation cycle which is measured by the heart-pulsation measuring device. With this arrangement, it is possible to obtain a frozen picture without any large blur even in the case of imaging of a portion which moves vehemently.

The above and other objects, features and advantages of the present invention will become apparent from the following description of the preferred embodiments thereof, taken in conjunction with the accompanying drawings.

BRIEF DESCRIPTION OF THE DRAWINGS

FIGS. 6A to 6E are charts which serve to illustrate each signal, such as a trigger signal, which is synchronized with the motion of the heart;

FIG. 8 is a circuit diagram which serves to illustrate the construction of a trigger-signal generating section in the first embodiment;

FIGS. 9a to 9d are views which serve to illustrate the operation of the trigger-signal generating section of FIG. 8;

FIGS. 10a to 10d are views which serve to illustrate examples of the pictures obtained by the first embodiment of the system according to the present invention;

FIG. 12 is a diagrammatic view showing the construction of an electronic endoscope and its associated portion which are used in the second embodiment.

DETAILED DESCRIPTION OF THE PREFERRED EMBODIMENTS

Figure 1:
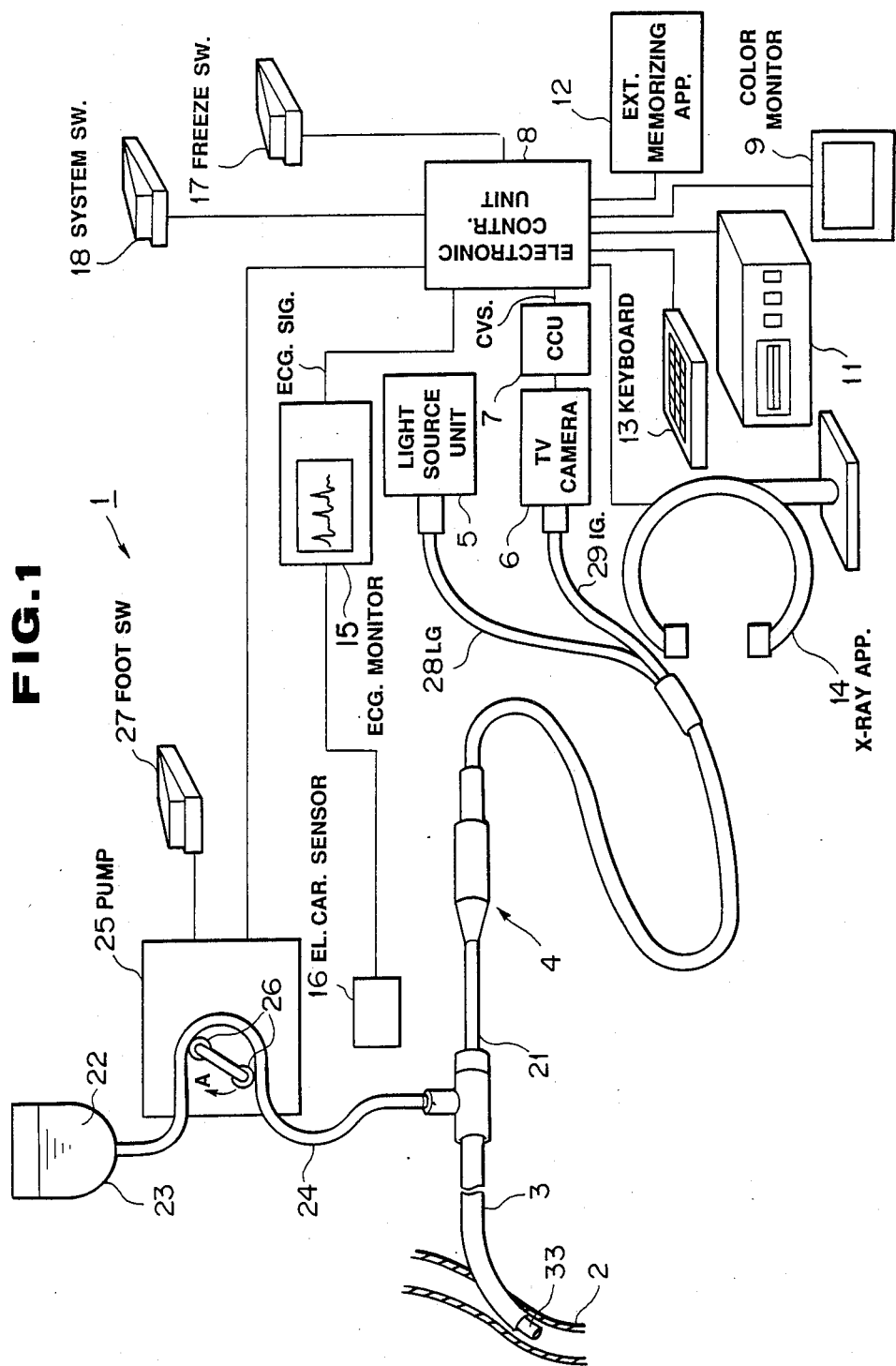
FIG. 1 is a schematic view showing the overall construction of a first embodiment of a system according to the present invention.

As shown in FIG. 1, a blood-vessel endoscope system 1 according to a first embodiment of the present invention includes a blood-vessel endoscope 4 which is capable of being inserted into a blood vessel 2 such as a coronary artery, the blood-vessel endoscope 4 being inserted through a sheath 3 provided for perfusion. One end of the blood-vessel endoscope 4 is connected to a light source unit 5 for supplying illumination light to the blood-vessel endoscope 4 and a television camera 6 for imaging an optical image transferred through the blood-vessel endoscope 4.

The television camera 6 is connected to a camera control unit (hereinafter referred to as the "CCU") 7 by a signal cable, and the CCU 7 effects signal processing for converting the image signal imaged by the television camera 6 into a standard video signal.

The output terminal of the CCU 7 is connected through an electronic control unit 8 to a color monitor 9 which serves as a display means, a color video printer 11 for printing out the picture displayed on the color monitor 9, and a storing apparatus 12 for memorizing video signals.

The electronic control unit 8 is further connected to a keyboard 13 which is used to input the data required to superimpose, for example, the name of a patient upon the endoscopic image displayed on the color monitor 9.

Also, the electronic control unit 8 is connected to an X-ray apparatus (or fluoroscope) 14 so that an X-ray image obtained from the X-ray apparatus 14 can be superimposed upon an endoscopic image displayed on the color monitor 9.

In addition, the electronic control unit 8 is connected to an electrocardiograph 15. The electrocardiograph 15 provides a display of the electrocardiographic waveform of a patient which is detected by an electrocardiographic sensor 16, and the obtained electrocardiographic signal is output to the electronic control unit 8. The electrocardiographic sensor 16 can be attached to, for example, the chest of the patient.

The electronic control unit 8 generates, from an incoming electrocardiographic signal, a trigger signal synchronized with the electrocardiographic waveform. When an operator actuates a freeze switch 17, the electronic control unit 8 provides control so as to cause the memorizing apparatus 12 to store an endoscopic image, etc. displayed on the color monitor 9 at a timing synchronized with the trigger signal. A switch 18 is provided for activating the blood-vessel endoscope system 1.

An inserting section 21 of the blood-vessel endoscope 3 is inserted through the sheath 3, and a gap through which a perfusate 22 can pass is defined between the sheath 3 and the inserting section 21. A perfusate reservoir 23 is connected to the trailing end of the sheath 3 by a flexible tube 24, and a pump 25 is connected to an intermediate portion of the tube 24. When the pump 25 is activated, a pair of pumping members 26 are caused to rotate in the direction indicated by an arrow A to apply squeezing pressure to the tube 24, thereby supplying the perfusate 22 to the leading end of the sheath 3.

The aforesaid pump 25 can be started and stopped by means of a foot switch 27. When the pump 25 is started, as shown in FIG. 6D, the state of fluid flow can be switched from a state (1) in which the flow of fluid stops to a state (2) in which an appropriate flow of fluid is supplied, and vice verse.

Figure 2:
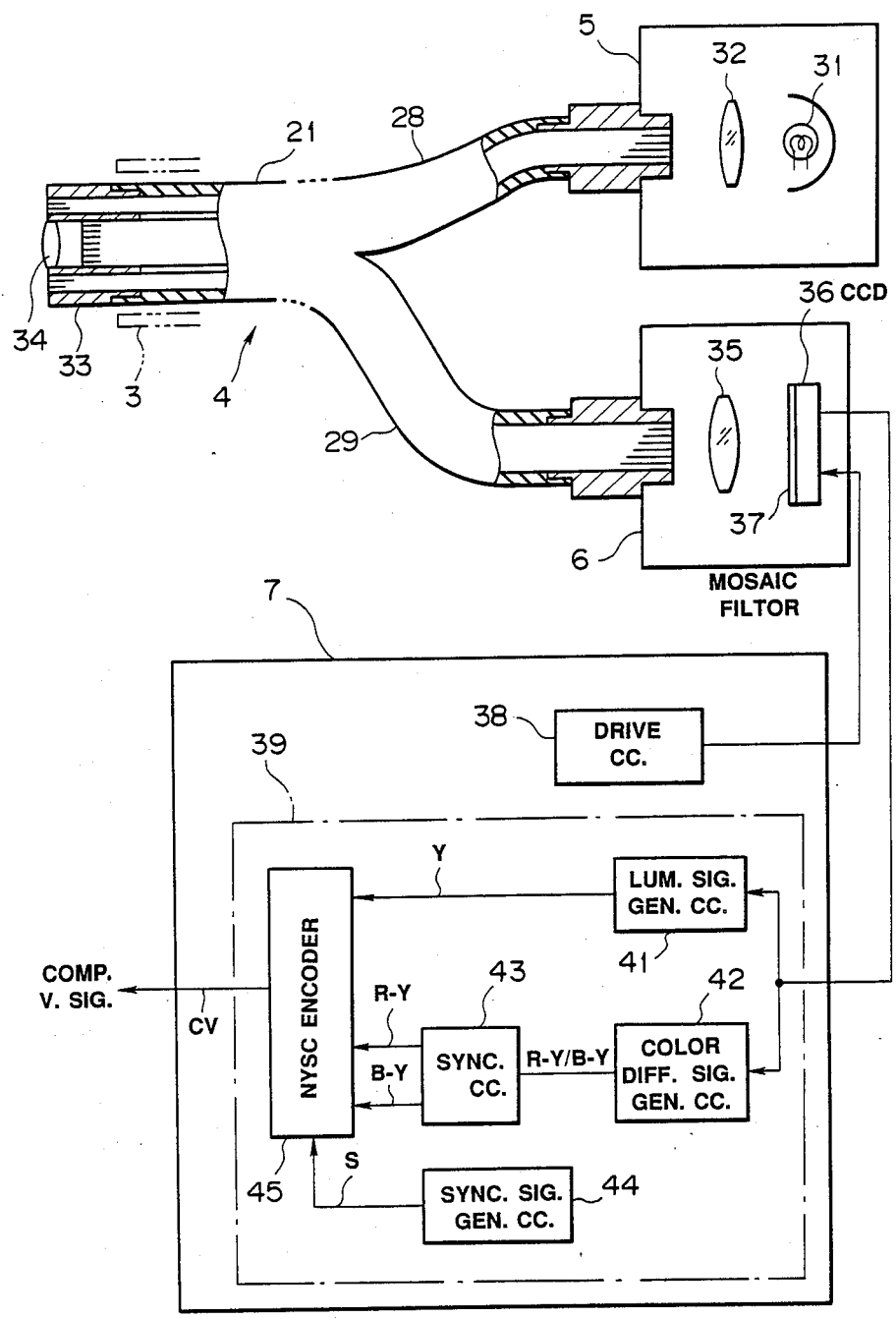
FIG. 2 is a diagrammatic view showing the construction of a blood-vessel endoscope and its associated portion which are used in the first embodiment.

The blood-vessel endoscope 4 is provided with the inserting section 21 which has a flexible and elongated body, and a light guide 28 and an image guide 29 are, as shown in FIG. 2, inserted through the inserting section 21, for example, in coaxial relationship with each other. The light guide 28 serves to transfer illumination light and the image guide 29 serves to transfer an optical image.

The light guide 28 and the image guide 29 are separated from each other at an intermediate location and are detachably connected to the light source unit 5 and the television camera 6, respectively.

The light source unit 5 is arranged so that the white light of a lamp 31 is focused on the entrance end surface of the light guide 28 by a condenser lens 32. The illumination light which is transferred through the light guide 28 is projected forwardly from the exit end surface which is secured at a leading end 33 of the inserting section 21. Thus, a portion to be observed is illuminated by the illumination light. An objective lens 34 is attached to the leading end 33 of the inserting section 21, and the entrance end surface of the image guide 29 is secured in the focal plane of the objective lens 34. An optical image of the aforesaid portion is focused on the entrance end surface of the image guide 29 by the objective lens 34. The optical image is then transferred from the entrance end surface to the exit end surface of the image guide 29. The optical image transferred to the exit end surface is focused, by a focusing lens 35, on the imaging surface of a CCD 36 which is disposed in the focal plane of the focusing lens 35. A color mosaic filter 37 for effecting color separation is attached to the front of the imaging surface, and the color of the optical image is separated by the filter 37.

The optical image focused on the CCD 36 is subjected to photo-electric conversion and accumulated as electric charge. Then, when a drive circuit 38 in the CCU 7 applies a drive signal to the CCD 36, the accumulated charge is read from the CCD 36, subjected to signal processing in a signal processing circuit 39, and converted into, for example, a composite video signal.

The signal processing circuit 39 is constituted by a luminance signal generating circuit 41 for generating a luminance signal Y from an input image signal, a color difference signal generating circuit 42 for generating line-sequential color difference signals R-Y and B-Y, a synchronizing circuit 43 for synchronizing the line-sequential color difference signals R-Y and B-Y, and an NTSC encoder 45 for generating a composite video signal from the synchronized color difference signals R-Y and B-Y, the luminance signal Y, and a synchronizing signal S output from a synchronizing signal generating circuit 44.

Figure 3:
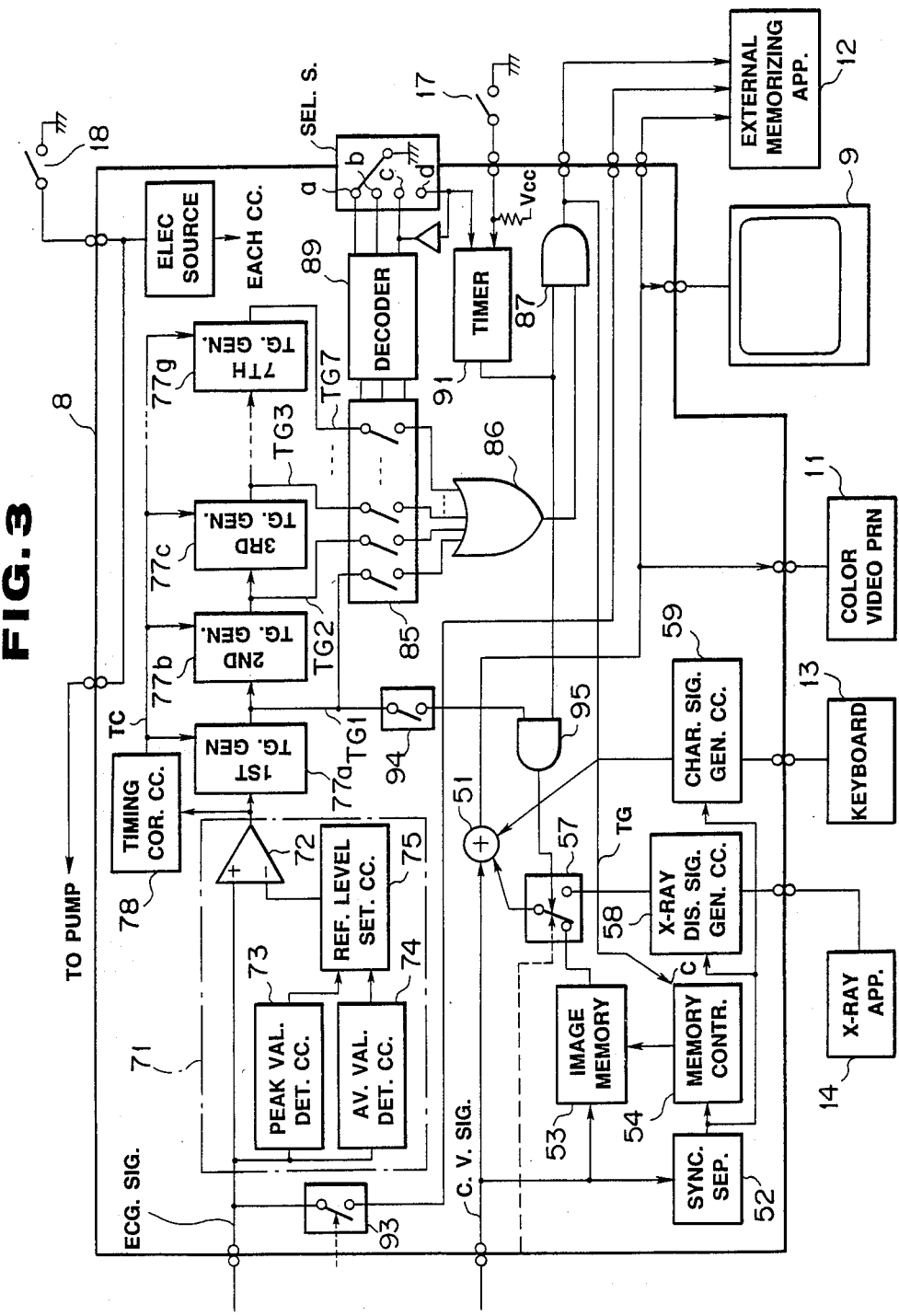
FIG. 3 is a block diagram showing the construction of an electronic control unit for use in the first embodiment.

FIG. 3 shows the diagrammatic construction of the electronic control unit 8 which receives various signals, such as a composite video signal CV output from the CCU 7.

The composite video signal CV from the CCU 7 is applied, through a mixer 51, to the respective video input terminals of the color monitor 9, the color video printer 11, and the external memorizing apparatus 1, as well as a synchronizing/separating circuit 52 and an image memory 53. The synchronizing signal which is extracted by separation in the synchronizing/separating circuit 52 is input to a memory control circuit 54. The image memory 53 stores the input composite video signal CV as a reduced frozen image under the control of the memory control circuit 54. For example, when a trigger signal TG is applied to a control terminal C of the memory control circuit 54, the memory control circuit 54 provides control so as to write a video signal for one frame/field into the image memory 53 in synchronization with the trigger signal.

Figure 4:
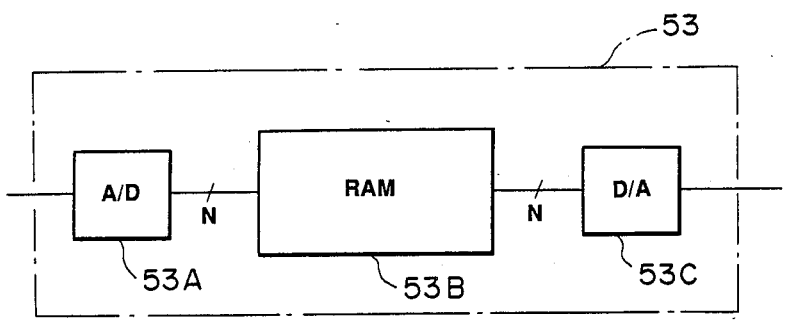
FIG. 4 is a schematic block diagram showing the construction of an image memory for use in the first embodiment.

As shown in FIG. 4, the image memory 53 is constituted by an A/D converter 53A for converting an analog signal into an N-bit digital signal, a semiconductor memory 53B constituted by a RAM for storing the digital signal, and a D/A converter 53C for converting the digital signal read from the semiconductor memory 53B into an analog signal.

The video signal written into the image memory 53 is read out by the memory control circuit 54 at a predetermined timing synchronized with the synchronizing signal.

Figure 5A:
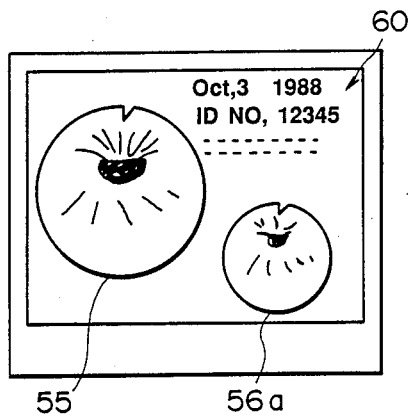
FIGS. 5a and 5b are views each of which show an example of an endoscopic image displayed on a monitor screen in accordance with the first embodiment.
Figure 5B:
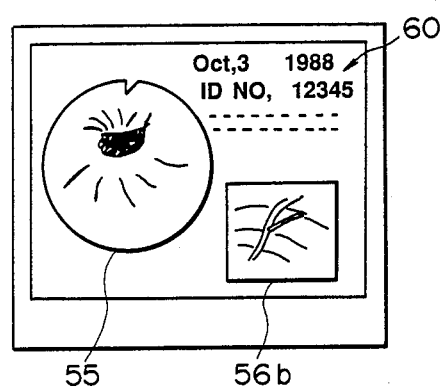

For example, the composite video signal CV output from the CCU 7 is, as shown in FIG. 5a, displayed as a circular real-time picture on the left-hand portion of the monitor screen of the color monitor 9. A reduced frozen picture 56a stored in the image memory 53, as shown in FIG. 5a, and an X-ray image 56b obtained by the X-ray apparatus 14, as shown in FIG. 5b, can be selectively displayed at a lower location on the right side of the real-time picture 55. This selection can be carried out by switching the signal level of the control terminal of an analog switch 57 to a high level or a low level.

The aforesaid X-ray apparatus 14 is used to check whether or not the blood-vessel endoscope 4 has been located at the desired portion.

During use, the X-ray apparatus 14 is set so as to clamp, for example, the chest of the patient.

The X-ray apparatus 14 is connected to an X-ray-display-signal generating circuit 58 which converts an X-ray image into a video signal and outputs the video signal at a predetermined timing in synchronization with the synchronizing signal. This output and the output of the image memory 53 are selectively supplied to the mixer 51 through the analog switch 57. In addition, the input signal from the keyboard 13 is input to the mixer 51 through a character-display-signal generating circuit 59. As shown in FIGS. 5a and 5b by way of example, such an input signal is displayed as patient data 60, for example, on the right side of the motion 55.

When the freeze switch 17 is actuated, a frozen picture is memorized in the external recording apparatus 12 in the following manner, in response to the trigger signal synchronized with the electrocardiographic waveform.

An electrocardiographic signal is input to a comparator 72, a peak-value detecting circuit 73, and an average-value detecting circuit 74, which are combined to constitute a reference pulse generating section 71.

The peak-value detecting circuit 73 and the average-value detecting circuit 74 detect the peak value and the average value of the electrocardiographic waveform, respectively. The peak value and the average value are input to a reference-level setting circuit 75, in which the peak value and the average value are averaged to obtain a reference level $V_{REF}$. If a signal having a level higher than the reference level $V_{REF}$ is input to the comparator 72, the comparator 72 outputs a binary-coded pulse.

Although, in this arrangement, the reference level $V_{REF}$ is generated using the average-value detecting circuit 74, the reference level $V_{REF}$ may be set at a level slightly lower than the output level of the peak-value detecting circuit 73.

Figure 7A:
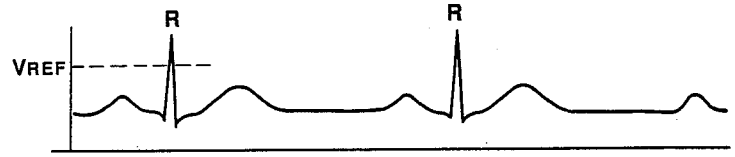
FIGS. 7a and 7b are charts which serves to illustrate the synchronization of a reference pulse signal with respect to an electrocardiographic waveform signal.
Figure 7B:

The aforesaid electrocardiographic signal, as shown in FIGS. 6A or 7a, has a waveform which exhibits its peak in accordance with the timing of each R wave. Accordingly, as shown in FIG. 7b, the reference pulse generating circuit 71 outputs a reference pulse $P_{ST}$ synchronized with the R wave.

The reference pulse $P_{ST}$ is input to a first trigger pulse generating section 77a, which generates a first trigger pulse TG1 when a predetermined time has elapsed after the trailing edge of the reference pulse $P_{ST}$. The first trigger pulse TG1 is input to a second trigger pulse generating section 77b, which generates a second trigger pulse TG2. In this fashion, the first trigger pulse TG1 to a seventh trigger pulse TG7 are generated. Each of the trigger pulse generating sections 77i (i=a, b, ..., g) is supplied with a timing correction signal TC in the timing correction circuit 78, thereby correcting the output timing of each trigger pulse TGj (j=1, 2, . . . , 7). More specifically, the period T of the reference pulse Pst shown in FIG. 7b is measured, and the trigger pulse generating sections 77i (i=a, b, ..., g) are controlled so that, as the period T is larger, the amount of delay of the timing of each trigger pulse TGj may increase. In other words, the output timing of each trigger pulse TGj is standardized in accordance with the period T so that the trigger pulse TGj may be output at a proper timing in correspondence with each patient having a different cycle of heart pulsation.

Each of the aforesaid trigger pulse generating generating sections 77i has the same construction (with a different time constant). FIG. 8 is a block diagram showing the construction of the first trigger pulse generating section 77a.

The reference pulse $P_{ST}$ is input to first and second one-shot multivibrators (hereinafter referred to as the "OSM(s)") 81a and 81b, and the first and second OSMs 81a and 81b are triggered by the trailing edge of the respective reference pulses $P_{ST}$. In response to the reference pulses $P_{ST}$, the pulse PL shown in FIG. 9b is provided at the output Q of the first OSM 81a and the pulse PS shown in FIG. 9c is provided at the output Q of the second OSM 82a. The pulses PL and PS are applied to an AND circuit 83a and the AND circuit 83a generates a first trigger pulse TG1 such as that shown in FIG. 9d.

The pulses PL and PS of the OSMs 81a and 82a are respectively determined by the time constant established by the capacitor Ca and the resistor r and the time constant established by the capacitor Ca' and the resistor r'. The resistors r and r' are selected by interlocked switches S1 and S1' from among the series resistors r1a, r2a and r3a; r1'a, r2'd and r3'a, respectively, and the OSMs 81a and 82a output the pulses PL and PS each having a time constant according to the corresponding selected resistor.

The selecting operations of the switches S1 and S1' are controlled by the timing correcting signal TC.

The timing pulse generating sections 77a to 77g respectively generate the trigger signals TG1 to TG7 of the pattern (1) shown in FIG. 6B. The trigger signals TG1 to TG7 are input to an analog switch 85 having a seven-circuit construction (FIG. 3) and the outputs of the analog switch 85 are input to an AND circuit 87 through a seven-input OR circuit 86.

The analog switch 85 is switched on and off by a decoder 89 on the basis of the digital data which is selected by a select switch SEL.S.

The select switch SEL.S has four contacts which enable four kinds of selection. If a first contact a is selected, all the switches of the analog switch 85 are switched on through the decoder 89. In this case, the first to seventh trigger signals TG1 to TG7 are output. In other words, a mode in which storing of an image is effected in each of seven periods during one cycle of heart pulsation shown in FIG. 6 is selected.

If a second contact b is selected, the mode of pattern 3 is selected in which the first, fourth and sixth trigger signals TG1, TG4 and TG6 are output.

If a third contact c is selected, the mode of pattern 3 is selected in which the first and fourth trigger signals TG1 and TG4 are output.

In each of the modes of patterns 1, 2 and 3, a frozen picture is stored only during the duration of a trigger gate signal which is output from a timer 91 and which is held in its high-level state during the period equal to or slightly shorter than the period T of one heart pulsation.

If a fourth contact d is selected, the mode of pattern 3 is selected and, at the same time, the timer 91 outputs a trigger gate signal which is held in the high-level state for a long time equivalent to several periods T. Accordingly, in this case, the first and fourth trigger signals TG1 and TG4 are output over a plurality of heat-pulsation cycles.

The output timings of the first and fourth trigger TG1 and TG4 are determined on the basis of an electrocardiographic waveform so as to be synchronized with the timing at which the motion of the myocardium comes to a halt immediately after each R wave and the period of isovolumetric relaxation which comes after each T wave.

Accordingly, even if each mode is selected, trigger signals used to start the operation of storing frozen pictures are applied to the release input terminal of the external memorizing apparatus 12 at timings including the above-described two timings. Thus, the frozen pictures are stored in synchronization with each of the trigger signals.

It is to be noted that the electrocardiographic signal can be applied through a switch 93 to an audio signal input terminal of the external memorizing apparatus 12 and a frozen picture and an electrocardiographic waveform can thus be stored.

Also, the first trigger signal TG1 is applied to the control terminal of the switch 57 through a switch 94 and an AND circuit 95. Thus, even where the switch 57 is switched to a contact corresponding to the image memory 53, when the switch 94 is switched on, then the switch 57 is switched to a contact corresponding to the X-ray-display-signal generating circuit 58 during the period in which the first trigger signal TG1 is input. Accordingly, in this case, the first trigger signal TG1 serves as a trigger signal, as shown in FIG. 6c, for storing an X-ray image. When this trigger signal TG1 is applied, a frozen picture such as that shown in, for example, FIG. 5b is stored together with the X-ray image.

If the electronic control unit 8 is constructed such that the first trigger signal TG1 and the fourth trigger signal TG4 are input to the AND circuit 95 through an OR circuit, an X-ray image can also be memorized in response to the trigger signal TG4 as shown by dashed lines in FIG. 6C.

In the first embodiment, if the release switch 17 is depressed when any one of the modes is selected, a plurality of frozen pictures are memorized at timings including at least the timing at which the action of the myocardium or the ventricle comes to a halt. Accordingly, it is possible to obtain a frozen picture without any large blur.

Accordingly, unlike the apparatus disclosed in the related art, it is possible to reduce the number of times of freezing operations.

In addition, it is possible to eliminate the necessity to supply an excessive amount of perfusate for the purpose of re-freezing.

Accordingly, it is possible to overcome the conventional problem that a large number of images must be memorized in order to obtain the desired frozen picture without any large blur. Furthermore, it is possible to reduce the number of times of freezing operations performed by an operator and to mitigate a pain which may be experienced by a patient due to the long-time freezing operation by the operator.

Since an X-ray image and an electrocardiographic waveform can be stored at the same time, the operator can make a precise analysis of an endoscopic image and an exact diagnosis by referring to both the X-ray image and the electrocardiographic waveform, as compared with a case where neither of them can be referred to.

When a frozen picture is stored with a constricted portion 102 of a myocardium 101 placed in the field of view as shown in FIGS. 10a and 10b, a frozen picture such as that shown in FIG. 10c which corresponds to an expansion period (the state shown in FIG. 10a) is obtained by the application of the fourth trigger signal TG4, while when the first trigger signal TG1 is applied, a frozen picture such as that shown in FIG. 10d which corresponds to a shrinking period (the state shown in FIG. 10b) is obtained. In other words, since it is possible to obtain an image corresponding to a position at which the myocardium 101 and the blood-vessel endoscope 4 are relatively displaced from each other to the maximum extent, the peripheral part of the constricted portion 102 of interest can be imaged over a wide area. Accordingly, when the symptom of the constricted portion 102 is to be diagnosed, sufficient data can be obtained and, therefore, a diagnosis can be easily made.

Figure 11:
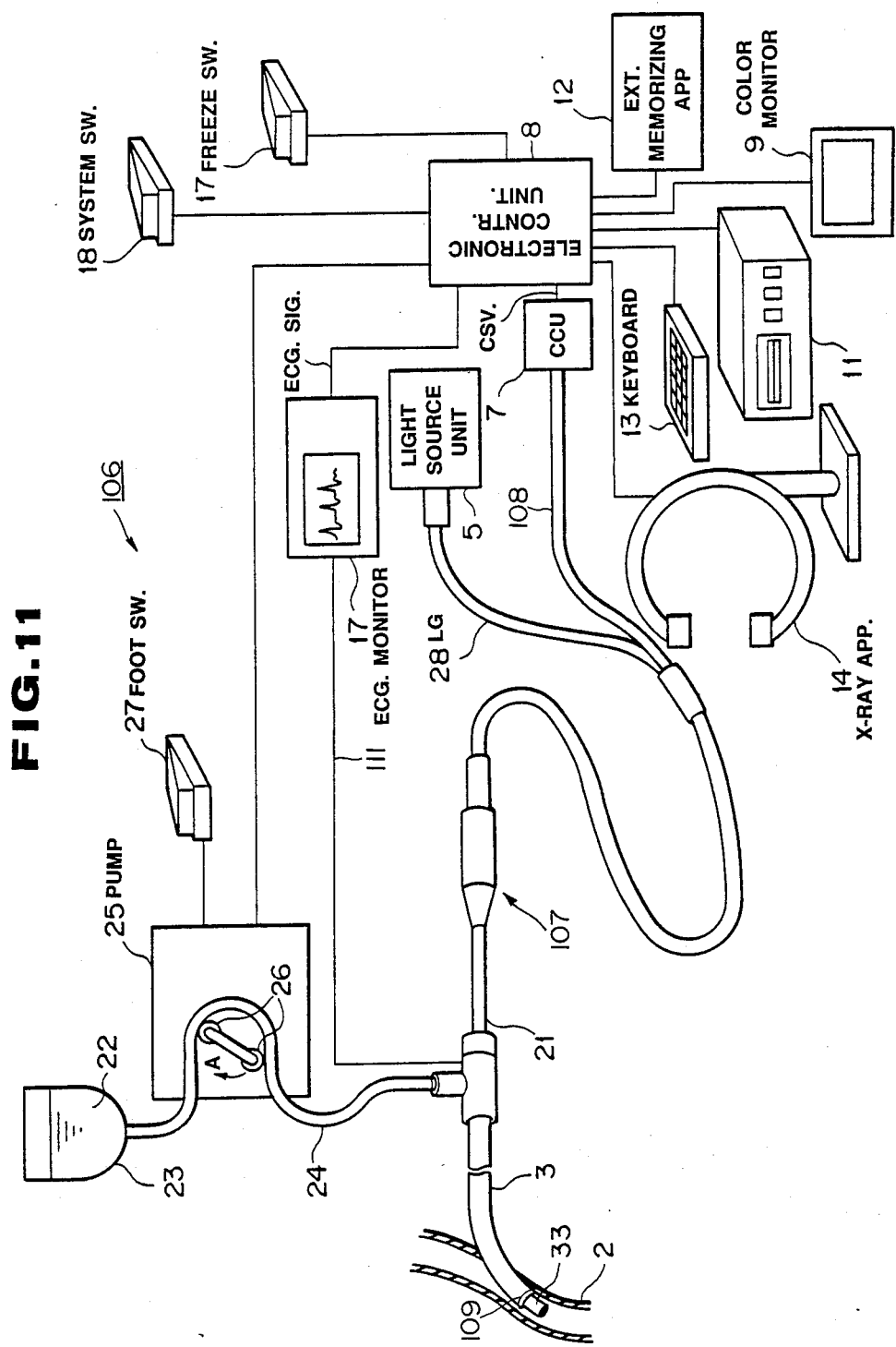
FIG. 11 is a schematic view showing the overall construction of a second embodiment of a system according to the present invention.

In the blood-vessel endoscope system 1 according to the first embodiment, the blood-vessel endoscope (fiber scope) 4 and the television camera 6 attached thereto are used as an imaging means. A blood-vessel endoscope system 106 according to the second embodiment shown in FIG. 11 uses an electronic scope 107 as an imaging means.

The electronic scope 107 does not have the image guide 29 used in the above-described blood-vessel endoscope 4 but, as shown in FIG. 12, a CCD 36' is located in the focal plane of an objective lens 34 disposed at the trailing end of an inserting section 21. A mosaic color filter 37' is attached to the front of the imaging surface of the CCD 36'. The CCD 36' is connected to the CCU 7 through the signal cable 108. The construction of the other portion is substantially identical to the construction of the corresponding portion of the aforesaid blood-vessel endoscope 4, and the description thereof will be omitted.

In this system 106, an electrocardiographic sensor 109 is attached to the leading end of the sheath 3, and the electrocardiographic sensor 109 is connected to the electrocardiographic monitor 17 through a cable (not shown) attached to the sheath 3 and a cable 111 extending from the trailing end of the sheath 3.

The construction of the other portion is substantially identical to that of the corresponding portion of the first embodiment, and the effects and advantages of the second embodiment are substantially identical to those of the first embodiment.

It is to be noted that, a cardiac-sound sensor may be used in place of the electrocardiographic sensor 109 and each trigger signal may be generated from the phonocardiographic waveform shown in FIG. 6A.

Figure 13:
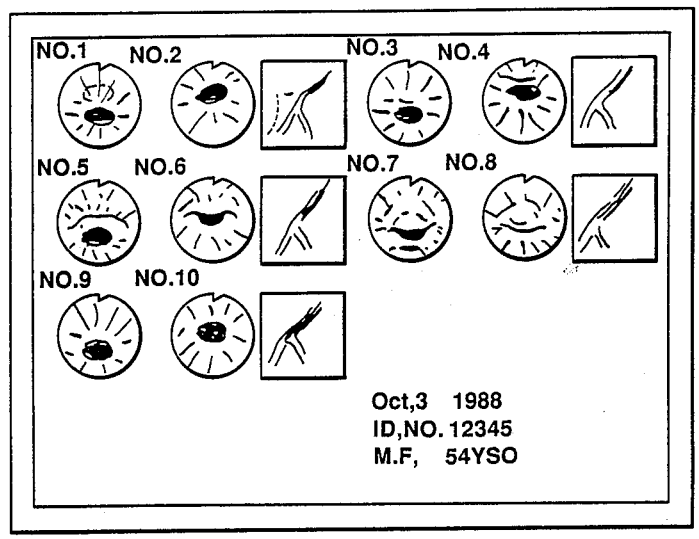
FIGS. 13 and 14 are views each of which shows the manner in which a plurality of frozen pictures are displayed on a monitor screen in accordance with the present invention.

In addition, in each of the above-described embodiments, after a preset number of (frames of) frozen pictures have been stored in the image memorizing apparatus 12, as shown in FIG. 13, a predetermined number of pictures may be displayed on an identical monitor screen at a time or continuously at an arbitrary speed.

Figure 14:
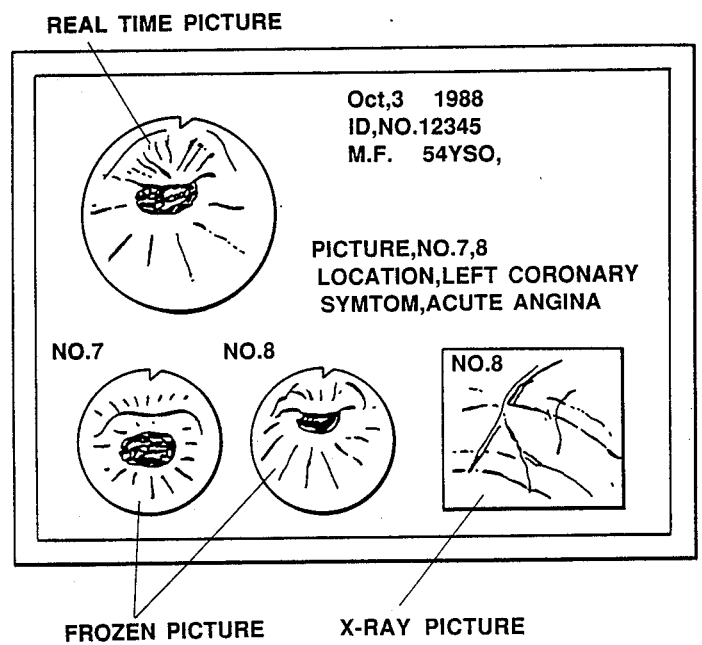

Furthermore, it is possible to adopt an arrangement in which, as shown in FIG. 14, while a real-time picture is being observed, for example, two pictures selected from among the frozen pictures stored in the image memorizing apparatus 12 are displayed together with an X-ray picture on an identical screen.

What is claimed is:
1. A blood-vessel endoscope system comprising:
    (a) an electronic endoscope including
        an inserting section inserted into a blood vessel in a living body,
        a light guide means, inserted through said inserting section, for transferring illumination light from a trailing end to a leading end and for emitting said illumination light from said leading end,
        an objective optical system disposed at the leading end of said inserting section focusing an object illuminated by said illumination light emitted from said leading end of said light guide means, and
        an imaging device photoelectrically converting an optical image obtained by said objective optical system;
    (b) light source means for supplying said illumination light to the trailing end of said light guide means;
    (c) a drive circuit outputting a drive signal to read a photoelectrically converted image signal from said imaging device;
    (d) a signal processing circuit for generating a standard video signal by signal processing said image signal read from said imaging device by applying said drive signal;
    (e) a color monitor displaying a picture from said video signal;
    (f) a heart pulsation measuring means for measuring heart pulsation of said living body;
    (g) frozen-picture memorizing means for storing, as a frozen picture, an endoscopic image obtained by imaging in said imaging device; and
    (h) frozen-picture release controlling means for generating, from a signal waveform output from said heart pulsation measuring means, a plurality of timing signals, during one cycle of heart pulsation, synchronized with said signal waveform and for then supplying said timing signals to a frozen-picture memorization controlling terminal of said frozen-picture memorizing means.

2. A blood-vessel endoscope system according to claim 1, wherein said frozen-picture release controlling means includes timing-signal outputting means for outputting said timing signals synchronized with said signal waveform.

3. A blood-vessel endoscope system according to claim 2, wherein said timing-signal outputting means is arranged to generate a timing signal including a reference timing signal which corresponds to a time that an action of a myocardium of said living body becomes the smallest.

4. A blood-vessel endoscope system according to claim 3, wherein said timing signal outputting means outputs another timing signal in addition to said reference timing signal.

5. A blood-vessel endoscope system according to claim 1, 2, 3 or 4, wherein said heart-pulsation measuring means is a heart-pulsation sensor which can be disposed at a leading end of a sheath into which said inserting section is inserted.

6. A blood-vessel endoscope system according to claim 1, 2, 3 or 4, wherein said heart-pulsation measuring means is an electrocardiograph.

7. A blood-vessel endoscope system according to claim 1, 2, 3, or 4; wherein said frozen-picture release controlling means includes release-period controlling means which enables said timing signal to be output during a period equivalent to a plurality of cycles of said signal waveform.

8. A blood-vessel endoscope system according to claim 1, 2, 3, 4, further comprising an X-ray apparatus and signal processing means for displaying, on said color monitor, an X-ray image obtained from said X-ray apparatus with said X-ray image superimposed upon the image obtained by imaging in said imaging device.

9. A blood-vessel endoscope system according to claim 8, wherein said frozen-picture memorizing means is capable of storing said X-ray image displayed on said color monitor.

10. A blood-vessel endoscope system according to claim 1, wherein said electronic endoscope includes an image guide fiber bundle inserted in said inserting section, one terminal of said image guide fiber bundle imaging an optical picture output by said objective optical system, and another of the terminals of said image guide fiber bundle mounted detachably to a television camera including said imaging device.

11. A blood-vessel endoscope system according to claim 1, wherein said electronic endoscope includes said imaging device disposed at the leading end of said inserting section.

12. A blood-vessel endoscope system according to claim 1, wherein said frozen-picture release controlling means is composed of a foot switch.

13. An endoscope system comprising:
(a) an electronic endoscope including
   an inserting section inserted into a body cavity in a living body,
   light guide means, inserted through said inserting section, for transferring illumination light from a proximal end to a distal end and for emitting said illumination light from said distal end,
   an objective optical system, disposed at the distal end of said inserting section, focusing an object illuminated by said illumination light emitted from said distal end of said light guide means, and
   an imaging device photoelectrically converting an optical image obtained by said objective optical system;
(b) light source means for supplying said illumination light to the proximal end of said light guide means;
(c) a drive circuit outputting a drive signal to read a photoelectrically converted image signal from said imaging device;
(d) a signal processing circuit generating a standard video signal by signal processing said image signal read from said imaging device by applying said drive signal;
(e) a color monitor displaying a picture from said video signal;
(f) a heart pulsation measuring means for measuring heart pulsation of said living body;
(g) frozen-picture memorizing means for storing, as a frozen picture, an endoscopic image obtained by imaging in said imaging device; and
(h) frozen-picture release controlling means for generating, from a signal waveform output from said heart pulsation means, a plurality of timing signals synchronized with said signal waveform and for then supplying said timing signals to a frozen-picture memorization controlling terminal of said frozen-picture memorizing means.

* * * * *